(12) United States Patent
Yoshitomo et al.

(10) Patent No.: US 8,816,135 B2
(45) Date of Patent: Aug. 26, 2014

(54) TRISPHENOL COMPOUND

(75) Inventors: Akira Yoshitomo, Wakayama (JP); Shihoko Nakano, Wakayama (JP)

(73) Assignee: Honshu Chemical Industry Co., Ltd., Tokyo (JP)

( * ) Notice: Subject to any disclaimer, the term of this patent is extended or adjusted under 35 U.S.C. 154(b) by 258 days.

(21) Appl. No.: 13/395,062

(22) PCT Filed: Sep. 9, 2010

(86) PCT No.: PCT/JP2010/065558
§ 371 (c)(1),
(2), (4) Date: Apr. 24, 2012

(87) PCT Pub. No.: WO2011/030835
PCT Pub. Date: Mar. 17, 2011

(65) Prior Publication Data
US 2012/0220805 A1  Aug. 30, 2012

(30) Foreign Application Priority Data
Sep. 9, 2009  (JP) ................................. 2009-208246

(51) Int. Cl.
C07C 39/14  (2006.01)
C07C 39/15  (2006.01)
C07C 37/20  (2006.01)

(52) U.S. Cl.
CPC ............... *C07C 39/15* (2013.01); *C07C 37/20* (2013.01)
USPC ........... 568/720; 568/716; 568/717; 568/722; 568/734

(58) Field of Classification Search
USPC .......................... 568/716, 717, 720, 722, 734
See application file for complete search history.

(56) References Cited

U.S. PATENT DOCUMENTS

| 5,650,262 | A | 7/1997 | Münzel et al. |
| 6,558,867 | B2 * | 5/2003 | Noda et al. ................ 430/191 |
| 6,703,181 | B1 * | 3/2004 | Hayashi et al. ........... 430/270.1 |
| 2008/0114183 | A1 * | 5/2008 | Moore et al. .................. 558/51 |
| 2010/0075253 | A1 | 3/2010 | Kato et al. |

FOREIGN PATENT DOCUMENTS

| EP | 0 599 799 A1 | 10/1993 |
| JP | 62-084035 A | 4/1987 |
| JP | 63-207817 A | 8/1988 |
| JP | 05-067701 A | 3/1993 |
| JP | 06-214388 A | 8/1994 |
| JP | 09-151149 A | 6/1997 |
| JP | 10-218814 A | 8/1998 |
| JP | 2003-300922 A | 10/2003 |
| JP | 2008-112134 A | 5/2008 |
| WO | WO 2007/142353 A1 | 12/2007 |
| WO | WO 2008/060735 A1 | 5/2008 |
| WO | WO 2008/072624 A1 | 6/2008 |

OTHER PUBLICATIONS

Silva; Chemistry of Materials; 2008, 20, 7292-7300.*
The International Search Report (ISR) by the Japanese Patent Office mailed on Oct. 12, 2010 issued for corresponding PCT patent application No. PCT/JP2010/065558.

* cited by examiner

*Primary Examiner* — Fereydoun G Sajjadi
*Assistant Examiner* — Pancham Bakshi
(74) *Attorney, Agent, or Firm* — Knobbe, Martens, Olson & Bear LLP

(57) ABSTRACT

A trisphenol compound is expressed by formula (1), wherein R represents an alkyl group or alkoxyl group with 1 to 8 carbon atoms, phenyl group or hydroxyl group; $R_1$ represents an alkyl group or alkoxyl group with 1 to 8 carbon atoms, or phenyl group; $R_2$ represents an alkyl group or alkoxyl group with 1 to 8 carbon atoms; $R_3$ represents a hydrogen atom or alkyl group with 1 to 8 carbon atoms; a represents 0, 1, 2, or 3; b represents 1 or 2; and c and d represent 0, 1, 2, 3, or 4; where the sum of b and c is 5 or less; R's may be either the same or different when a is 2 or more; $R_1$'s may be either the same or different when c is 2 or more; and $R_2$'s may be either the same or different when d is 2 or more.

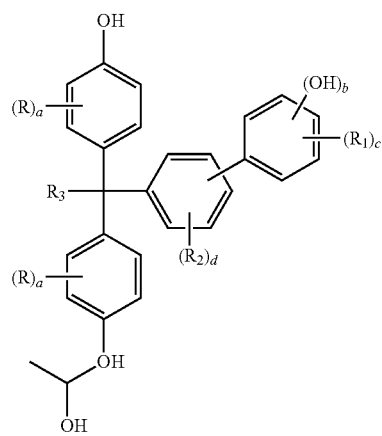

(1)

2 Claims, No Drawings

TRISPHENOL COMPOUND

This application is the U.S. National Phase under 35 U.S.C. §371 of International Application PCT/JP2010/065558, filed Sep. 9, 2010, which claims priority to Japanese Patent Application No. 2009-208246, filed Sep. 9, 2009. The International Application was published under PCT Article 21(2) in a language other than English.

TECHNICAL FIELD

The present invention relates to a novel trisphenol compound, and more specifically to a novel trisphenol compound having a hydroxyphenyl group directly bonded, in the form of single bond, to the phenyl nucleus of the phenylalkylidene group at the center of the molecule.

PRIOR ART

Trisphenol compounds have traditionally been used in wide ranging applications as a material for photosensitive resist, material for epoxy resins used in electric insulation materials, etc., branching agent for aromatic polycarbonate, developer material, and anti-fade agent material used for thermosensitive recording materials, and also as a material for germicide, sterilizing antifungal agent, etc.

As such trisphenol compounds as above, for example, trisphenol compounds having various kinds of structures, such as 1-[α-methyl-α-(4'-hydroxyphenyl)ethyl]-4-[α',α'-bis(4"-hydroxyphenyl)ethyl]benzene (hereinafter also referred to as "TrisP-PA") (Patent Literature 1), 2,2'-[(4-hydroxy-3-methoxyphenyl)methylene]bis[3,5-dimethylphenol] or other trisphenol compounds where the phenol nucleus has an alkoxy group (Patent Literature 2), and 4,4'-[(2-hydroxyphenyl)methylene]bis[2,3,6-trimethylphenol] or other trisphenol compounds having three methyl groups on two phenyl nuclei (Patent Literature 3), etc. are known.

In recent years, however, various characteristics such as levels of sensitivity, resolution, residual film ratio, heat resistance, storage stability and the like achieved for photosensitive resist materials, especially positive resist materials, are not necessarily satisfactory, and there is a strong demand for performance improvement through trisphpenols having new structures.

PRIOR ART LITERATURES

Patent Literatures

Patent Literature 1: Japanese Patent Laid-open No. Sho 62-084035
Patent Literature 2: Japanese Patent Laid-open No. Hei 10-218815
Patent Literature 3: Japanese Patent Laid-open No. Hei 09-151149

SUMMARY OF THE INVENTION

Problems to be Resolved by the Invention

The present invention was developed against the aforementioned background surrounding trisphenols, and it is the object of the present invention to provide a trisphenol compound which offers excellent solubility in organic solvents used for photosensitive resist, etc., and is expected to improve heat resistance if used as photosensitive resist material, etc.

Means for Solving the Problems

After studying in earnest to solve the aforementioned problems, the inventors have found that solubility in organic solvents and/or heat resistance (glass transition temperature) will unexpectedly improve to a significant degree when a trisphenol is created based on the structure whereby trisphenol having a conventional structure such as TrisP-PA changed in such a way that the single bond was used as the bonding group between the phenyl nucleus at the center of the molecule and the hydroxyphenyl nucleus at the end of the molecule, in place of the 2,2-propylidene group, and completed the present invention accordingly.

In other words, the present invention provides a trisphenol compound represented by general formula (1):

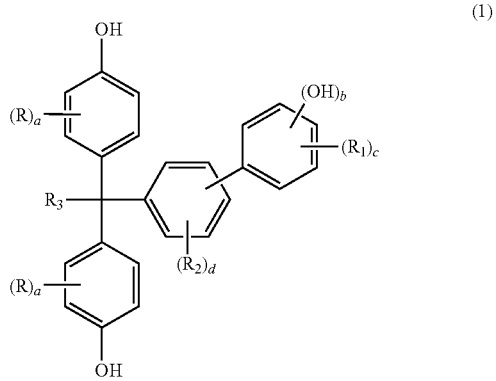

(in the formula, R represents an alkyl group with 1 to 8 carbon atoms, alkoxyl group with 1 to 8 carbon atoms, phenyl group or hydroxyl group; $R_1$ represents an alkyl group with 1 to 8 carbon atoms, alkoxyl group with 1 to 8 carbon atoms or phenyl group; $R_2$ represents an alkyl group with 1 to 8 carbon atoms or alkoxyl group with 1 to 8 carbon atoms; $R_3$ represents a hydrogen atom or alkyl group with 1 to 8 carbon atoms; a represents 0 or an integer of 1 to 3; b represents an integer of 1 or 2; and c and d represent 0 or an integer of 1 to 4; where the sum of b and c is 5 or less; R's may be either the same or different when a is 2 or more; $R_1$'s may be either the same or different when c is 2 or more; and $R_2$'s may be either the same or different when d is 2 or more).

A preferred embodiment of the present invention is a trisphenol compound expressed by general formula (2), which is the same as general formula (1) above except that substituents $(R)_a$ are indicated by $R_4$, $R_5$ and $R_6$:

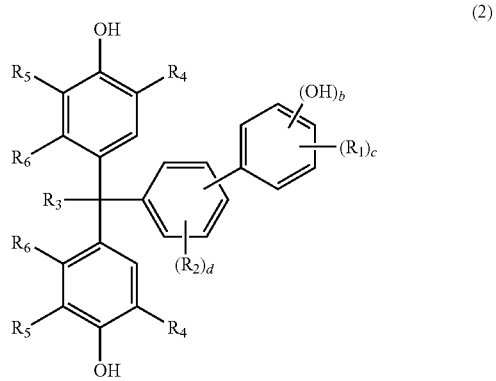

(in the formula, each $R_4$, $R_5$ and $R_6$ may be either the same or different and each represents a hydrogen atom, alkyl group with 1 to 8 carbon atoms, alkoxyl group with 1 to 8 carbon atoms, phenyl group or hydroxyl group; while $R_1$, $R_2$, $R_3$, b, c and d are the same as the corresponding items in general formula (1)).

A more preferred embodiment of the present invention is a trisphenol compound expressed by general formula (3), which is the same as general formula (1) above except that substituents $(R)_a$ are indicated by $R_4$, $R_5$ and $R_6$ and b is 1:

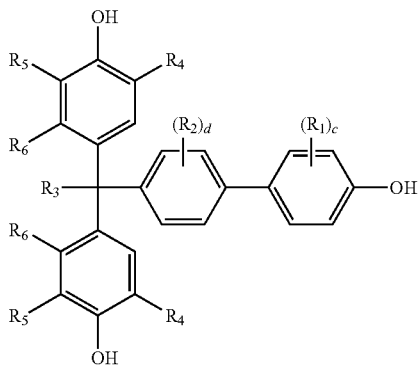

(3)

(in the formula, $R_1$, $R_2$, $R_3$, $R_4$, $R_5$, $R_6$, c and d are the same as the corresponding items in general formula (2)).

Effects of the Invention

A trisphenol compound according to the present invention is a compound constituted by two hydroxyphenyl groups bonding via a phenylalkylidene group substituted by other hydroxyphenyl group. Such trisphenol compound offers excellent heat resistance (high glass transition temperature) and/or solubility in a range of solvents used in the field of photoresist, and by changing the structure of substituents, it can answer diverse demands for heat resistance and solubility levels more easily than conventionally known trisphenols such as 1-[α-methyl-α-(4-hydroxyphenyl)ethyl]-4-[α,α-bis (4-hydroxyphenyl)ethyl]benzene and the like.

Also, when used in a photosensitive resist composition, even when a large amount of a trisphenol compound according to the present invention or derivative thereof is used, it does not precipitate easily from the solvent and, because the heat resistance of the resist itself improves, improved resolution and excellent effects on the sensitivity or storage stability of resist solution can be expected. Accordingly, the present invention can be used favorably as a quinonediazidesulfonic acid ester compound in the photosensitizer material for positive resist, or directly as an additive for resist. It can also be used favorably as a branching agent for synthetic resins such as aromatic polycarbonate resins and the like, a material for epoxy resins used in electric insulation materials, etc., and the like.

MODES FOR CARRYING OUT THE INVENTION

Regarding a trisphenol compound expressed by general formula (1) below as proposed by the present invention,

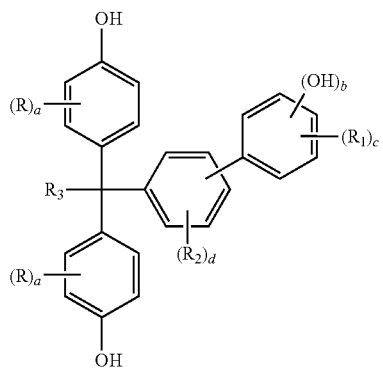

(1)

in the formula, R represents an alkyl group with 1 to 8 carbon atoms, alkoxyl group with 1 to 8 carbon atoms, phenyl group or hydroxyl group, while a represents 0 or an integer of 1 to 3, where, when a is 2 or more, R's may be either the same or different. Here, the alkyl group with 1 to 8 carbon atoms may be a straight, branched or cyclic alkyl group and, if R is an alkyl group with 1 to 8 carbon atoms, the alkyl group may be substituted by one or two phenyl groups or alkoxyl groups or may not be substituted at all. Note, however, that preferably the 1-position of the alkyl group is not substituted by an alkoxyl group. A preferred form is a straight or branched alkyl group with 1 to 4 carbon atoms or cycloalkyl group with 5 to 8 carbon atoms.

Specific examples of the alkyl group with 1 to 8 carbon atoms include, for example, methyl group, ethyl group, propyl group, isopropyl group, butyl group, t-butyl group, cyclohexyl group, cyclopentyl group, etc., as well as benzyl group being a substitution alkyl group.

Also, the alkoxyl group with 1 to 8 carbon atoms may be a straight, branched or cyclic alkoxyl group, and any such alkoxyl group may be substituted by one or two phenyl groups or may not be substituted at all. A preferred form is a straight or branched alkoxyl group with 1 to 4 carbon atoms or cycloalkoxyl group with 5 to 8 carbon atoms. Specific examples of the alkoxyl group with 1 to 8 carbon atoms include, for example, a methoxy group, ethoxy group, propoxy group, t-butoxy group, cyclohexyloxy group and cyclopentyloxy group, etc.

If a phenyl group is used, the phenyl group may be substituted by one to three alkyl groups with 1 to 8 carbon atoms and/or alkoxyl groups with 1 to 8 carbon atoms. Specific examples include, for example, phenyl group, 4-methylphenyl group and 4-methoxyphenyl group, etc. Preferably the number of such substituents is 0 or 1.

Preferably a (the number of R substitutions) is 0, 1 or 2. If a is 1 or 2, the substitution position of R is preferably the o-position of the hydroxyl group.

Also, if a is 1 or more and at least one R is a hydroxyl group or phenyl group, the number of hydroxyl or phenyl group substitutions is preferably 1 or 2, and more preferably is 1. Also, if a is 1 or more, at least one R is a hydroxyl group and if the number of hydroxyl group substitutions is 1, the substitution position is preferably the 3-position of the 4-hydroxyphenyl group, or the 2-position and 3-position if the number of hydroxyl group substitutions is 2. If the hydroxyl group substitution position is the 2-position, $R_3$ is preferably a hydrogen atom. Also, if a is 1 or more, at least one R is a phenyl group and the number of phenyl group substitutions is 1, the substitution position is preferably the 3-position or 5-position of the 4-hydroxyphenyl group, or 3-position and 5-position if the number of phenyl group substitutions is 2.

Also regarding a trisphenol compound expressed by general formula (1), in the formula, $R_3$ represents a hydrogen atom or alkyl group with 1 to 8 carbon atoms and, if it is an alkyl group with 1 to 8 carbon atoms, it is a straight or branched alkyl group or is preferably a straight or branched alkyl group with 1 to 4 carbon atoms. Also, for the alkyl group, a primary or secondary alkyl group is preferred. Specific examples of the alkyl group with 1 to 8 carbon atoms include, for example, methyl group, ethyl group, propyl group, isopropyl group, butyl group and isobutyl group, etc.

Also in the formula, $R_1$ represents an alkyl group with 1 to 8 carbon atoms, alkoxyl group with 1 to 8 carbon atoms or phenyl group, while c represents 0 or an integer of 1 to 4, and, if c is 2 or more, $R_1$ may be either the same or different. Here, if $R_1$ is an alkyl group with 1 to 8 carbon atoms, alkoxyl group with 1 to 8 carbon atoms or phenyl group, as the alkyl group, alkoxyl group, or phenyl group, it is the same as the aforementioned alkyl group with 1 to 8 carbon atoms, alkoxyl group with 1 to 8 carbon atoms or phenyl group for R, respectively, and the alkyl group is preferably an alkyl group with 1 to 4 carbon atoms such as methyl group or the like, or cycloalkyl group with 5 to 8 carbon atoms, while the alkoxyl group is preferably an alkoxyl group with 1 to 4 carbon atoms such as methoxy group or the like or cycloalkoxyl group with 5 to 8 carbon atoms. The number of substituents c is preferably 0 or 1 to 3, or more preferably 0 or 1.

Also in the formula, $R_2$ represents an alkyl group with 1 to 8 carbon atoms or alkoxyl group with 1 to 8 carbon atoms, while d represents 0 or an integer of 1 to 4, and, if d is 2 or more, $R_2$'s may be either the same or different. Here, if $R_2$ is an alkyl group with 1 to 8 carbon atoms, as the alkyl group, it is the same with the aforementioned alkyl group with 1 to 8 carbon atoms for $R_3$, and preferably is straight or branched alkyl group with 1 to 4 carbon atoms such as methyl group and the like. If it is an alkoxyl group with 1 to 8 carbon atoms, as the alkoxyl group, it is a straight or branched alkoxyl group. Preferably it is a straight or branched alkoxyl group with 1 to 4 carbon atoms, and specific examples include, for example, a methoxy group, ethoxy group, propoxy group and t-butoxy group, etc.

The number of substituents d is preferably 0 or 1 to 3, or more preferably 0 or 1.

Accordingly, a preferred form of the trisphenol compound expressed by general formula (1) is expressed by general formula (2) below where the substituents $(R)_a$ are indicated by $R_4$, $R_5$ and $R_6$:

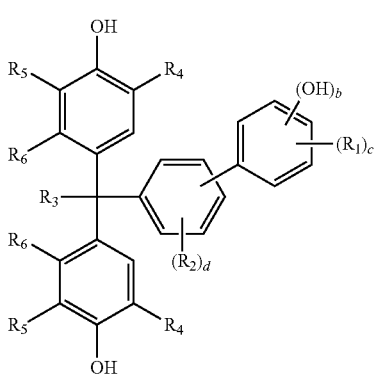

(2)

In the formula, each $R_4$, $R_5$ and $R_6$ may be either the same or different and each independently represents a hydrogen atom, alkyl group with 1 to 8 carbon atoms, alkoxyl group with 1 to 8 carbon atoms, phenyl group or hydroxyl group. If $R_3$ is an alkyl group, $R_6$ is preferably a hydrogen atom; while if $R_6$ is not a hydrogen atom, $R_3$ is preferably a hydrogen atom. If $R_6$ is not a hydrogen atom, $R_6$ is preferably an alkyl group, or more preferably a methyl group.

If at least one of $R_4$, $R_5$ and $R_6$ is a hydroxyl group, the preferred number of hydroxyl group substitutions or substitution positions are the same as the number of substitutions or substitution positions when R in general formula (1) above is a hydroxyl group. Accordingly, preferably $R_4$ and $R_5$ are not a hydroxyl group at the same time and, if the number of hydroxyl group substitutions is 1, preferably either $R_4$ or $R_5$ is a hydroxyl group; while, if the number of hydroxyl group substitutions is 2, preferably $R_3$ is a hydrogen atom and $R_5$ and $R_6$ are a hydroxyl group.

If at least one of $R_4$, $R_5$ and $R_6$ is a phenyl group, as the phenyl group, it is the same as the phenyl group for R in general formula (1) above, and the preferred number of phenyl group substitutions or substitution positions are also the same. Accordingly, if the number of phenyl group substitutions is 1, preferably either $R_4$ or $R_5$ is a phenyl group; while, if the number of phenyl group substitutions is 2, preferably $R_4$ and $R_5$ are a phenyl group.

Even when $R_4$, $R_5$ and $R_6$ are an alkyl group and/or alkoxyl group, as the alkyl group or alkoxyl group, it is the same as the alkyl group and/or alkoxyl group for R in general formula (1) above, where a straight or branched alkyl group or alkoxyl group with 1 to 4 carbon atoms, or cycloalkyl group or cycloalkoxyl group with 5 to 8 carbon atoms, is preferred.

As for the combination of $R_4$, $R_5$ and $R_6$, preferably all are a hydrogen atom, or $R_4$ and/or $R_5$ is/are a group other than hydrogen atom and other group(s) is/are a hydrogen atom, where the group other than hydrogen atom is preferably an alkyl group. If both $R_4$ and $R_5$ are an alkyl group, preferably at least one or both is/are a primary or secondary alkyl group. More preferably $R_4$ and $R_4$ are the same, $R_5$ and $R_5$ are the same, and $R_6$ and $R_6$ are the same.

Also in the formula, each $R_1$, $R_2$, $R_3$, b, c and d are the same as the corresponding items in general formula (1), respectively, where b is preferably 1.

The substitution position of the hydroxyphenyl group at which substitution of $R_1$ is permitted in general formula (1) and general formula (2) is preferably the p-position or m-position, or more preferably the p-position, relative to the bis (4-hydroxyphenyl)methyl group substituted by $R_3$.

The substitution position of the hydroxyl group on the hydroxyphenyl group at which substitution of $R_1$ is permitted in general formula (1) and general formula (2) is preferably the p-position and/or m-position, or more preferably the p-position if the number of substitutions (b) is 1, relative to the substitution position of the phenylene group at the center of the molecule.

A more preferred form of the trisphenol compound expressed by general formula (1) is expressed by general formula (3) below where the substituents $(R)_a$ are indicated by $R_4$, $R_5$ and $R_6$ and b is 1:

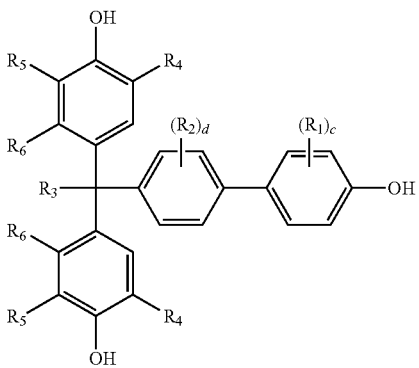

(3)

(in the formula, $R_1$, $R_2$, $R_3$, $R_4$, $R_5$, $R_6$, c and d are the same as the corresponding items in general formula (2), respectively).

Specific examples of such trisphenol compound include, for example:

1-[4-(4-hydroxyphenyl)phenyl]-1,1-bis(4-hydroxyphenyl)ethane;

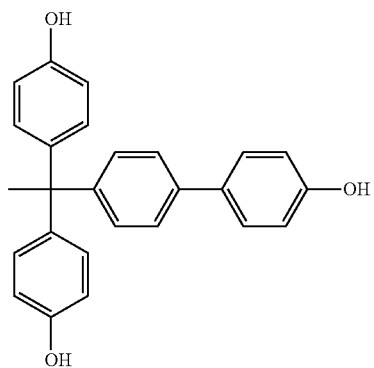 [SMILES: CC(c1ccc(O)cc1)(c1ccc(O)cc1)c1ccc(-c2ccc(O)cc2)cc1]

1-[4-(4-hydroxyphenyl)phenyl]-1,1-bis(4-hydroxy-3-methylphenyl)ethane;

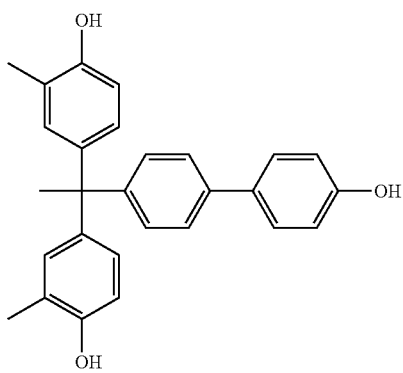 [SMILES: Cc1cc(C(C)(c2ccc(-c3ccc(O)cc3)cc2)c2ccc(O)c(C)c2)ccc1O]

1-[4-(4-hydroxyphenyl)phenyl]-1,1-bis(4-hydroxy-3,5-dimethylphenyl)ethane;

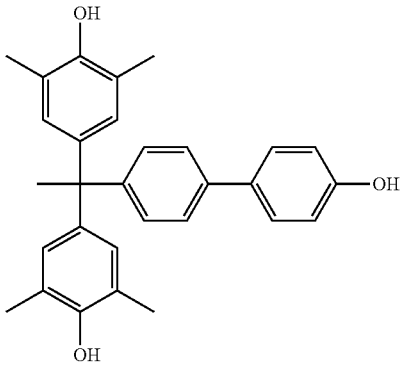 [SMILES: Cc1cc(C(C)(c2ccc(-c3ccc(O)cc3)cc2)c2cc(C)c(O)c(C)c2)cc(C)c1O]

1-[4-(4-hydroxyphenyl)phenyl]-1,1-bis(4-hydroxy-3-ethylphenyl)ethane;
1-[4-(4-hydroxyphenyl)phenyl]-1,1-bis(4-hydroxy-3-isopropylphenyl)ethane;
1-[4-(4-hydroxyphenyl)phenyl]-1,1-bis(4-hydroxy-3-cyclohexylphenyl)ethane;
1-[4-(4-hydroxyphenyl)phenyl]-1,1-bis(4-hydroxy-3-methoxyphenyl)ethane;
1-[4-(4-hydroxyphenyl)phenyl]-1,1-bis(4-hydroxy-3-phenylphenyl)ethane;
1-[4-(4-hydroxyphenyl)phenyl]-1,1-bis(4-hydroxyphenyl)propane;
1-[4-(4-hydroxyphenyl)phenyl]-1,1-bis(4-hydroxy-3-methylphenyl)propane;
1-[4-(4-hydroxyphenyl)phenyl]-1,1-bis(4-hydroxy-3,5-dimethylphenyl)propane;
1-[4-(4-hydroxy-3-methylphenyl)phenyl]-1,1-bis(4-hydroxyphenyl)ethane;
1-[4-(4-hydroxy-3-methylphenyl)phenyl]-1,1-bis(4-hydroxy-3-methylphenyl)ethane;
1-[4-(4-hydroxy-3-methylphenyl)phenyl]-1,1-bis(4-hydroxy-3,5-dimethylphenyl)ethane;
1-[4-(4-hydroxy-3-methoxyphenyl)phenyl]-1,1-bis(4-hydroxyphenyl)ethane;
1-[4-(4-hydroxy-3-methoxyphenyl)phenyl]-1,1-bis(4-hydroxy-3-methylphenyl)ethane;
1-[4-(4-hydroxy-3-methoxyphenyl)phenyl]-1,1-bis(4-hydroxy-3,5-dimethylphenyl)ethane;
1-[4-(4-hydroxyphenyl)phenyl]-1,1-bis(4-hydroxy-2,3,5-trimethylphenyl)methane;
1-[4-(4-hydroxyphenyl)phenyl]-1,1-bis(4-hydroxy-2,5-dimethylphenyl)methane;
1-[3-(4-hydroxyphenyl)phenyl]-1,1-bis(4-hydroxyphenyl)methane;
1-[3-(4-hydroxyphenyl)phenyl]-1,1-bis(4-hydroxyphenyl)ethane;
1-[4-(4-hydroxyphenyl)phenyl]-1-(4-hydroxy-3-methylphenyl)-1-(4-hydroxy-3,5-dimethylphenyl)ethane;
1-[4-(4-hydroxyphenyl)phenyl]-1-(4-hydroxyphenyl)-1-(4-hydroxy-3-methylphenyl)ethane;
1-[4-(4-hydroxy-3-methoxyphenyl)phenyl]-1-(4-hydroxyphenyl)-1-(4-hydroxy-3-methylphenyl)ethane; and
1-[4-(4-hydroxy-3-methoxyphenyl)phenyl]-1-(4-hydroxyphenyl)-1-(4-hydroxy-3,5-dimethylphenyl)ethane, etc.

The method for manufacturing the trisphenol compound expressed by general formula (1) above as proposed by the present invention is not specifically limited, and it can be obtained according to known manufacturing methods such as those described in Japanese Patent Laid-open No. Hei 10-17510, Hei 9-176068, etc., by, for example, causing a carbonyl compound expressed by general formula (4) to react with a phenols expressed by general formula (5) in the presence of an acid catalyst, as shown in reaction formula (1).

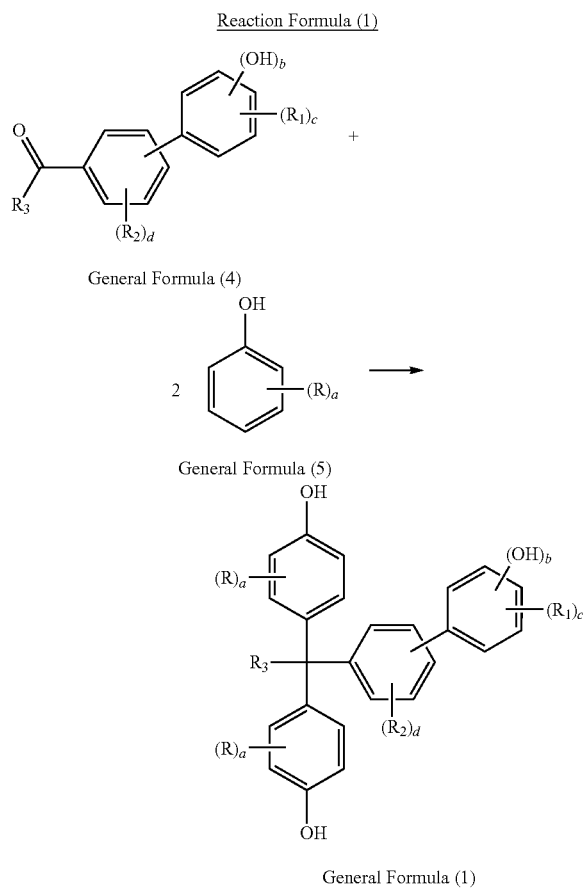

As for the carbonyl compound expressed by general formula (4), $R_1$, $R_2$, $R_3$, b, c and d in the formula are the same as the corresponding items in general formula (1).

Also for the phenols expressed by genera formula (5), R and a in the formula are the same as the corresponding items in general formula (1). If a is 1 or more, however, R is not substituted at the p-position of the hydroxyl group.

Also in general formula (5), a preferred phenols corresponding to general formula (2) above is expressed by general formula (6) below:

General Formula (6)

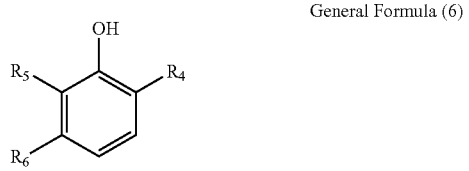

(in the formula, $R_4$, $R_5$, and $R_6$ are the same as the corresponding items in general formula (2)).

When manufacturing a trisphenol compound under the present invention, specific examples of the carbonyl compound expressed by general formula (4) above include, for example, 4-acetyl-4'-hydroxybiphenyl, 4-propionyl-4'-hydroxybiphenyl, 4-formyl-3'-phenyl-4'-hydroxybiphenyl, 4-acetyl-3'-ethyl-4'-hydroxybiphenyl, 3-acetyl-4'-hydroxybiphenyl, 4-formyl-4'-hydroxybiphenyl and 3-formyl-4'-hydroxybiphenyl, etc.

Also, specific examples of the phenols expressed by general formula (5) or general formula (6) include, for example, phenol, o-cresol, 2,6-xylenol, 2-isopropylphenol, 2-cyclohexylphenol, 2-methoxyphenol, 2-phenylphenol, 2,5-xylenol, 2-cyclohexyl-5-methylphenol, 2,3,6-trimethylphenol, catechol, 3-methylcatechol, 4-methylcatechol and resorcin, etc.

Any of these phenols may be used alone or two or more types may be used at the same time. If, in the case of a bis(hydroxyphenyl)alkyl group, compounds having two hydroxyphenyl groups each having different R's, R substitution positions and/or a's (the number of R substitutions) need to be obtained, then two or more types of phenols may be used at the same time.

The method for manufacturing a trisphenol compound expressed by general formula (1) as proposed by the present invention is explained in greater detail.

To obtain a trisphenol compound expressed by general formula (1), a carbonyl compound expressed by general formula (4) above which corresponds to the structure of the target trisphenol compound, and phenols expressed by general formula (5), may be used as materials.

At the time of reaction, the phenols expressed by general formula (5) is used normally by 2 mol times or more, or preferably in a range of 3 to 20 mol times, or more preferably in a range of 4 to 12 mol times, relative to the carbonyl compound expressed by general formula (4).

Also, specific preferable examples of the aforementioned acid catalyst include, for example, inorganic acids such as hydrogen chloride gas, hydrochloric acid, sulfuric acid, phosphoric acid, sulfuric anhydride and the like, organic acids such as p-toluenesulfonic acid, methanesulfonic acid, trifluoromethanesulfonic acid, oxalic acid, formic acid, trichloroacetic acid and the like, and solid acids such as acid ion-exchange resin and the like, etc. In particular, hydrogen chloride gas or hydrochloric acid is preferred.

The additive amount of such acid catalyst cannot be generalized because an appropriate amount varies depending on the catalyst. In the case of 35% hydrochloric acid, for example, normally it is used in a range of 1 to 20 parts by weight relative to 100 parts by weight of the material phenols. In the case of hydrogen chloride gas, a preferable method is to first saturate hydrogen chloride gas in the aforementioned material phenols or in a solution or slurry constituted by the phenols and solvent, and then cause the reaction under flowing hydrochloric acid gas.

To promote the reaction, a co-catalyst may be used as necessary. Particularly when $R_3$ is an alkyl group in the material carbonyl compound expressed by general formula (4), normally it is preferable to use a co-catalyst as it improves the yield. Examples of such co-catalyst include, for example, mercaptans such as methylmercaptan, ethylmercaptan, octylmercaptan, dodecylmercaptan and the like, and mercaptoacetic acid, etc. If methylmercaptan is used, it may be used in the form of an aqueous sodium salt solution. The amount of co-catalyst (when 15% aqueous sodium salt solution of methylmercaptan is used) is normally in a range of 1 to 50 percent by weight, or preferably in a range of 10 to 40 percent by weight, relative to the carbonyl compound expressed by general formula (4).

At the time of reaction, no solvent needs to be used if the material phenol is in liquid form at the reaction temperature, but if the material phenol is in solid form at the reaction temperature, or if necessary to make the material carbonyl compound into a solution form or slurry form, it is preferable to use a solvent. Any solvent can be used as long as it remains inert during the reaction, but examples include, e.g., lower aliphatic alcohols such as methanol, ethanol and the like, hydrocarbons such as toluene, xylene, hexane and the like, ethers such as tetrahydrofuran, dioxolane and the like, or water if a phenols such as catechol that easily dissolves in water is used. Lower aliphatic alcohols such as methanol, ethanol and the like are preferred. Only one type of such solvent may be used or two or more types may be mixed together.

The amount of solvent used is not specifically limited, but it is normally 0.1 to 10 parts by weight, or preferably in a range of 0.5 to 5 parts by weight, or more preferably in a range of 0.8 to 2 parts by weight, relative to one part by weight of the material carbonyl compound; however, the amount is not limited to the foregoing.

The reaction is implemented at temperatures normally in a range of 0° C. to 90° C., or preferably in a range of 10° C. to 70° C., or more preferably in a range of 20° C. to 50° C. The reaction needs to occur normally for around 1 to 72 hours, or preferably for around 3 to 12 hours, with agitation under flowing nitrogen.

After the reaction, alkali such as ammonia water, aqueous sodium hydroxide solution or the like is added to the obtained reaction liquid to neutralize the acid catalyst, after which a solvent such as an aromatic hydrocarbon or the like that separates from water is added, and then the water layer is separated to obtain the oil layer, and the obtained oil layer is cooled and crystallized, or precipitated and then filtered out, to obtain crystal or solid. It is also possible to remove the solvent and unreacted phenols out of the aforementioned oil layer by distillation, and then dissolve the residual liquid in a solvent to cause crystallization. It is also possible to add a solvent to the aforementioned solution after the neutralization of the acid catalyst, followed by crystallization and cooling without further treatment, or to wash further with water the aforementioned oil layer obtained upon separating the water layer and then cool and crystallize the oil layer, or precipitate the oil layer, followed by filtration. If the required purity of the target compound is high, the crystal or solid obtained above can be refined using a known method such as recrystallization, reprecipitation or the like. This way, the target trisphenol compound can be obtained at high purity with ease.

Also, the method for manufacturing the material carbonyl compound expressed by general formula (4) is not specifically limited, and it can be manufactured according to a known manufacturing method such as the one described in Japanese Patent Laid-open No. Sho 63-130565, etc. For example, if the material carbonyl compound is expressed by general formula (4), where the biphenyl is substituted by one hydroxyl group and acyl group at the 4-position and 4'-position, respectively, then, as shown in reaction formula (2) below, the material carbonyl compound can be manufactured by using a 4-phenylphenols expressed by general formula (7) as the material and acylating the material as shown in general formula (8) and general formula (9), followed by hydrolysis and/or alcoholysis.

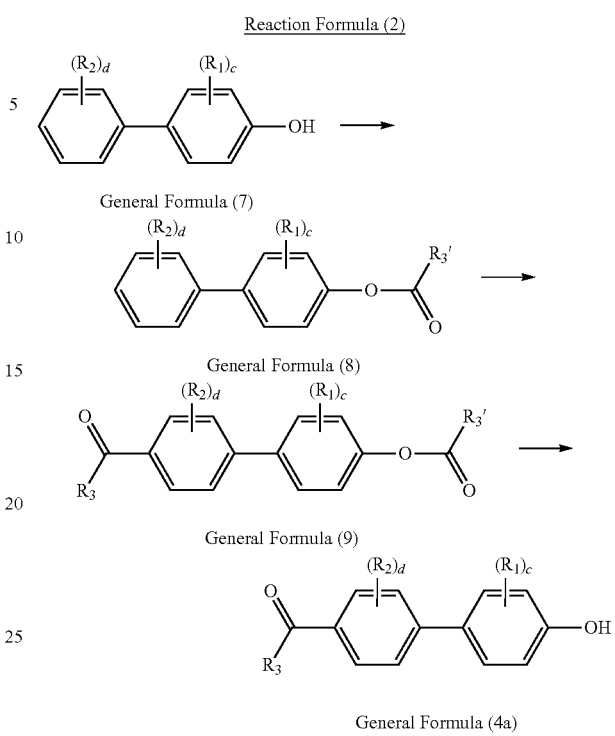

(In the formula, $R_1$, $R_2$, $R_3$, c and d are the same as the corresponding items in general formula (1), while $R_3'$ is the same as $R_3$ in general formula (1).)

When the method indicated by reaction formula (2) is described in further detail, a 4-hydroxybiphenyls expressed by general formula (7) such as 4-phenylphenol, 2-methyl-4-phenylphenol, 4-(3-methylphenyl)phenol, 4-(3-isopropylphenyl)phenol, 4-(2-methylphenyl)phenol, 4-(2,6-dimethylphenyl)phenol, 4-(2-methylphenyl)-2-methylphenol, 4-(2-methylphenyl)-3-methylphenol, 4-phenyl-2,3,6-trimethylphenol, 2-methoxy-4-phenylphenol or the like is caused to react with a halogenated acyl expressed by general formula (10) such as an acetyl chloride in the presence of a base such as pyridine or the like, or caused to be acylated using an excess amount of an acid anhydride expressed by general formula (11) such as acetic anhydride, to synthesize a 4-acyloxybiphenyls expressed by general formula (8) above.

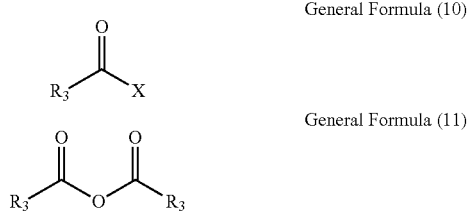

(In the formula, $R_3$ is the same as the corresponding item in general formula (1), while X represents a halogen atom.)

Next, the obtained 4-acyloxybiphenyls is caused to react further with a complex obtained by mixing a halogenated acyl expressed by general formula (10) or acid anhydride expressed by general formula (11) and Lewis acid such as aluminum chloride, to obtain a 4-acyl-4'-acyloxybiphenyl compound expressed by general formula (9), and when this is then hydrolyzed and/or alcoholyzed using alkali, a material carbonyl compound expressed by general formula (4a) can be manufactured at high purity with ease.

Also, another manufacturing method is, for example, to cause an acylphenylboronic acids expressed by general formula (12) to react with a halogenated phenols expressed by general formula (13) in the presence of tetrakis(triphenylphosphine) palladium and sodium carbonate, as shown in reaction formula (3) below, as this allows for manufacturing of a material carbonyl compound expressed by general formula (4) at high purity with ease.

Reaction Formula (3)

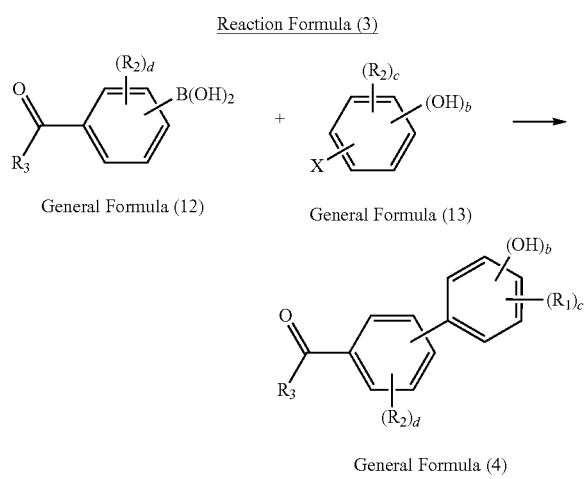

General Formula (12)

General Formula (13)

General Formula (4)

(In the formula, $R_1$, $R_2$, $R_3$, b, c and d are the same as the corresponding items in general formula (1), while X represents a halogen atom.)

EXAMPLE (1) Measurement Method for Glass Transition Temperature

Each compound was heated to a temperature 20° C. higher than the melting point of the compound in crystal form using a differential scanning calorimeter, and the melted compound was cooled and then heated again to measure the glass transition point. The measurement conditions were 40° C. as the temperature at which to start measurement, the melting point+20° C. as the temperature at which to end measurement, and 10.0° C./min. as the rate of heating.

(2) Measurement Method for Solubility in Solvent

As for solubility, 10 g of propyleneglycolmonomethylether acetate was put in a container and 1 g of trisphenol compound was added while keeping the temperature at 28° C., and the mixture was agitated for 10 minutes to check for complete dissolution of the compound. If the compound had dissolved fully, 1 g was added in the same manner and dissolved, and this operation was repeated until the compound no longer dissolved. The solubility (amount in grams per 100 g of solvent) was calculated from the largest amount of compound in grams that dissolved completely.

Reference Example 1

Synthesis of 4-acetyl-4'-hydroxybiphenyl in Material Carbonyl Compound (Synthesis of 4-acetoxybiphenyl Into a 3-liter, 4-way flask equipped with a reflux cooling tube, 373.8 g of acetic anhydride and 248.0 g (1.46 mol) of 4-phenylphenol were introduced and the mixture was heated to cause reaction for 3 hours under agitation while keeping the temperature in the flask at 130° C. After the reaction, the reflux pipe was replaced with a distillation pipe and acetic anhydride and acetic acid were removed by distillation under decompression, after which n-heptane was added and the mixture was cooled. The precipitated crystal was filtered out and dried to obtain 296.8 g of 4-acetoxybiphenyl in a white crystal form. The yield relative to the material 4-phenylphenol was 96% (mol).

Synthesis of 4-acetyl-4'-hydroxybiphenyl

Into a 3-liter, 4-way flask equipped with a reflux device and drip funnel, 314 g of aluminum chloride and 628 g of chloroform were introduced, and 120 g of acetic anhydride was dripped into the mixture under agitation over a period of 1 hour while keeping the temperature in the flask at 5 to 15° C. Furthermore, a liquid mixture of 100.0 g of the 4-acetoxybiphenyl obtained above and 200 g of chloroform was dripped under agitation over a period of 3 hours while keeping the temperature at 4 to 7° C. When the entire volume had been dripped, the mixture was caused to react for 2 hours under agitation while keeping the temperature at 4 to 7° C.

After the reaction, distilled water was added and the mixture was agitated fully, and then the water layer was separated and removed. Water was added to the obtained oil layer and the mixture was agitated, followed by separating and removing the water layer, and this water wash operation was performed several times. The solvent was condensed and methanol was added to dissolve the residue, and then 84.0 g of 28% sodium methylate methanol solution was dripped under agitation while keeping the temperature at 45° C., and the reaction was continued further for 1 hour at the same temperature. After the reaction, acetic acid was added to neutralize the reaction mixture, after which distilled water was added and the mixture was cooled. The precipitated crystal was filtered out and dried to obtain 87.6 g of 4-acetyl-4'-hydroxybiphenyl. The yield relative to the 4-acetoxybiphenyl was 88% (mol).

Example 1

Synthesis of 1-[4-(4-hydroxyphenyl)phenyl]-1,1-bis(4-hydroxyphenyl)ethane

Into a 500-ml, 4-way flask equipped with an agitator, reflux cooler tube and drip funnel, 6.8 g of methanol and 46.0 g (0.489 mol) of phenol were introduced, and the interior of the flask was replaced with hydrogen chloride gas, after which hydrogen chloride gas was blown in until saturation. Thereafter, 9.0 g of 21% aqueous sodium salt solution of methylmercaptan was dripped under agitation over a period of 1.5 hours while keeping the temperature in the flask at 30 to 35° C. Furthermore, a liquid mixture prepared by dissolving 30.0 g (0.141 mol) of the 4-acetyl-4'-hydroxybiphenyl obtained in Reference Example 1 into 60.0 g (0.637 mol) of phenol and 25 g of methanol was dripped under agitation over a period of 1 hour while keeping the temperature in the flask at 30 to 35°

C. When the entire volume had been dripped, the mixture was caused to react further for 2.5 hours under agitation while keeping the temperature in the flask at 30° C.

After the reaction, the reaction mixture was neutralized with 16% aqueous sodium hydroxide solution and the water layer was separated, after which 90 g of toluene and 100 g of water were added to the oil layer, followed by agitation and water wash, and the water layer was separated. Water was added to wash the obtained oil layer, followed by separating the water layer, and this operation was repeated several times more. The reflux cooler tube was replaced with a distillation pipe and the solvent was distilled, after which phenol was removed by distillation under decompression, and then a liquid mixture of methylisobutylketone and toluene was added to the remaining residues to cause crystallization, and the precipitated crystal was filtered out. Methylethylketone and ethylbenzene were added to the obtained crystal and the mixture was heated and dissolved, after which it was cooled and crystallized. The precipitated crystal was filtered out and dried under decompression to obtain 18.0 g of 1-[4-(4-hydroxyphenyl)phenyl]-1,1-bis(4-hydroxyphenyl)ethane in a white solid form. The yield relative to the material 4-acetyl-4'-hydroxybiphenyl was 33% (mol).

Purity: 99.3% (High-speed liquid chromatography)

Molecular weight: 382 (M-H)$^-$ (Liquid chromatography mass spectrometry)

Melting point: 198° C. (Differential scanning calorimeter (DSC) method)

Glass transition temperature: 98° C.

Solubility: 40 g/100 g of propyleneglycolmonomethylether acetate $^1$H-NMR (400 MHz) measurement (Solvent: DMSO-d6)

TABLE 1

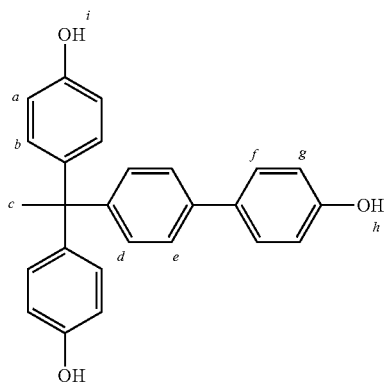 [SMILES: CC(c1ccc(O)cc1)(c1ccc(O)cc1)c1ccc(-c2ccc(O)cc2)cc1]

$^1$H-NMR (400 MHz) identification results (Internal reference: Tetramethylsilane)

| Shift value (ppm) | Number of protons | Signal | Assignment |
| --- | --- | --- | --- |
| 2.05 | 3 | s | c |
| 6.68-6.76 | 4 | d | a |
| 6.79-6.91 | 6 | m | b, g |
| 7.05-7.10 | 2 | d | d |
| 7.48-7.49 | 4 | m | e, f |
| 9.36 | 2 | s | i |
| 9.58 | 1 | s | h |

Example 2

Synthesis of 1-[4-(4-hydroxyphenyl)phenyl]-1,1-bis(4-hydroxy-3-methylphenyl)ethane Into a 500-ml, 4-way flask equipped with an agitator, reflux cooler tube and drip funnel, 6.3 g of methanol and 61.0 g (0.564 mol) of o-cresol were introduced, and the interior of the flask was replaced with hydrogen chloride gas, after which hydrogen chloride gas was blown in until saturation. Thereafter, 9.0 g of 21% aqueous sodium salt solution of methylmercaptan was dripped under agitation over a period of 1.5 hours while keeping the temperature in the flask at 30 to 35° C. Furthermore, a liquid mixture prepared by dissolving 30.0 g (0.141 mol) of the 4-acetyl-4'-hydroxybiphenyl obtained in Reference Example 1 into 60.0 g (0.555 mol) of o-cresol and 30 g of methanol was dripped under agitation over a period of 2 hours while keeping the temperature in the flask at 30 to 35° C. When the entire volume had been dripped, the mixture was caused to react further for 2 hours under agitation at 30° C.

After the reaction, the reaction mixture was neutralized with 16% aqueous sodium hydroxide solution and the water layer was separated. 100 g of toluene and 100 g of water were added to the obtained oil layer, followed by agitation and water wash, followed by separating the water layer. Thereafter, the oil layer was cooled and precipitated crystal was filtered out to obtain crude crystal. The crude crystal was recrystallized using a mixed solvent of toluene and methylisobutylketone and then filtered out and refined, after which the refined crystal was further recrystallized using a mixed solvent of methylethylketone and ethylbenzene and then filtered out to obtain 19.3 g of 1-[4-(4-hydroxyphenyl)phenyl]-1,1-bis(4-hydroxy-3-methylphenyl)ethane (Adduct with Methylethylketone) in a Light Red Solid Form Purity: 98.2% (High-speed liquid chromatography)

Molecular weight: 410 (M-H)$^-$ (Liquid chromatography mass spectrometry)

$^1$H-NMR (400 MHz) measurement (Solvent: DMSO-d6)

TABLE 2

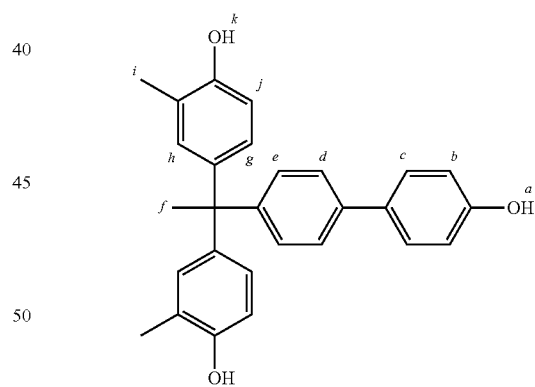

$^1$H-NMR (400 MHz) identification results (Internal reference: Tetramethylsilane)

| Shift value (ppm) | Number of protons | Signal | Assignment |
| --- | --- | --- | --- |
| 2.01 | 3 | s | f |
| 2.04 | 6 | s | i |
| 6.60-6.66 | 4 | m | g, h |
| 6.79-6.98 | 4 | m | b, j |
| 7.03-7.05 | 2 | d | e |
| 7.44-7.47 | 4 | m | c, d |
| 9.10 | 2 | s | k |
| 9.49 | 1 | s | a |

Example 3

Synthesis of 1-[4-(4-hydroxyphenyl)phenyl]-1,1-bis(4-hydroxy-3,5-dimethylphenyl)ethane Into a 500-ml, 4-way flask equipped with an agitator, reflux cooler tube and drip funnel, 11.4 g of methanol and 100.0 g (0.819 mol) of 2,6-xylenol were introduced, and the interior of the flask was replaced with hydrogen chloride gas, after which hydrogen chloride gas was blown in until saturation. Thereafter, 9.0 g of 21% aqueous sodium salt solution of methylmercaptan was dripped under agitation over a period of 1.5 hours while keeping the temperature in the flask at 35 to 37° C. Furthermore, a liquid mixture prepared by dissolving 30.0 g (0.141 mol) of the 4-acetyl-4'-hydroxybiphenyl obtained in Reference Example 1 into 38.0 g (0.311 mol) of 2,6-xylenol and 30 g of methanol was dripped under agitation over a period of 1 hour while keeping the temperature in the flask at 35 to 40° C. When the entire volume had been dripped, the mixture was caused to react further for 14 hours under agitation at 40° C.

After the reaction, the reaction mixture was neutralized with 16% aqueous sodium hydroxide solution and heated, after which 144.6 g of methanol was added, the mixture was cooled, and the precipitated crystal was filtered out to obtain crude crystal. The crude crystal was recrystallized using methylisobutylketone to obtain 50.6 g of 1-[4-(4-hydroxyphenyl)phenyl]-1,1-bis(4-hydroxy-3,5-dimethylphenyl)ethane of 99.2% in purity (according to high-speed liquid chromatography) in a white solid form. The yield relative to the material 4-acetyl-4'-hydroxybiphenyl was 81% (mol).

Molecular weight: 437 (M-H)⁻ (Liquid chromatography mass spectrometry)

Melting point: 231° C. (Differential scanning calorimeter (DSC) method)

Glass transition temperature: 104° C.

Solubility: 10 g/100 g of propyleneglycolmonomethylether acetate $^1$H-NMR (400 MHz) measurement (Solvent: DMSO-d6)

TABLE 3

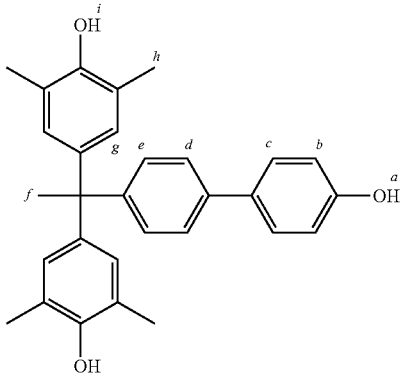 [SMILES: Cc1cc(C(C)(c2ccc(-c3ccc(O)cc3)cc2)c2cc(C)c(O)c(C)c2)cc(C)c1O]

$^1$H-NMR (400 MHz) identification results (Internal reference: Tetramethylsilane)

| Shift value (ppm) | Number of protons | Signal | Assignment |
|---|---|---|---|
| 2.00 | 3 | s | f |
| 2.07 | 12 | s | h |
| 6.60 | 4 | s | g |
| 6.81-6.84 | 2 | d | b |
| 7.03-7.05 | 2 | d | e |
| 7.44-7.48 | 4 | m | c, d |
| 8.04 | 2 | s | i |
| 9.50 | 1 | s | a |

Comparative Example

Measurement of glass transition temperature and solubility of 1-[α-methyl-α-(4-hydroxyphenyl)ethyl]-4-[α,α-bis(4-hydroxyphenyl)ethyl]benzene Glass transition temperature: 96° C.

Solubility: 10 g/100 g of propyleneglycolmonomethylether acetate

What is claimed is:

1. A trisphenol compound of general formula (1):

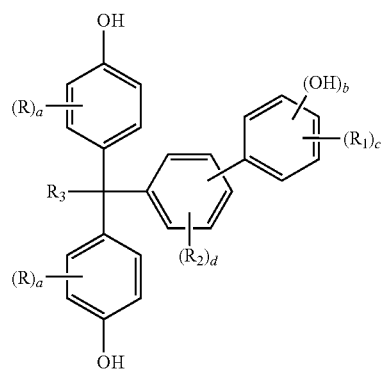

(in the formula, R represents an alkyl group with 1 to 8 carbon atoms, alkoxyl group with 1 to 8 carbon atoms, phenyl group or hydroxyl group; $R_1$ represents an alkyl group with 1 to 8 carbon atoms, alkoxyl group with 1 to 8 carbon atoms or phenyl group; $R_2$ represents an alkyl group with 1 to 8 carbon atoms or alkoxyl group with 1 to 8 carbon atoms; $R_3$ represents a hydrogen atom or alkyl group with 1 to 8 carbon atoms; a represents 0 or an integer of 1 to 3; b represents an integer of 1 or 2; and c and d represent 0 or an integer of 1 to 4; where the sum of b and c is 5 or less; R's may be either the same or different when a is 2 or more; $R_1$'s may be either the same or different when c is 2 or more; and $R_2$'s may be either the same or different when d is 2 or more).

2. The trisphenol compound according to claim 1, of general formula (3):

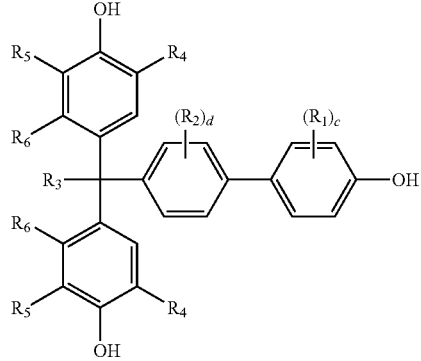

(in formula (3), each $R_4$, $R_5$ and $R_6$ may be either the same or different and each represents a hydrogen atom, alkyl group with 1 to 8 carbon atoms, alkoxyl group with 1 to 8 carbon atoms, phenyl group or hydroxyl group; while $R_1$, $R_2$, $R_3$, c and d are the same as the corresponding items in general formula (1)).

* * * * *